(12) United States Patent
Yu

(10) Patent No.: US 8,480,736 B2
(45) Date of Patent: Jul. 9, 2013

(54) SILICONE ARTIFICIAL BREAST PROSTHESIS WHICH MINIMIZES STRESS CONCENTRATION, AND PRODUCTION METHOD THEREFOR

(76) Inventor: Won-Seok Yu, Daejeon (KR)

( * ) Notice: Subject to any disclaimer, the term of this patent is extended or adjusted under 35 U.S.C. 154(b) by 0 days.

(21) Appl. No.: 13/443,064

(22) Filed: Apr. 10, 2012

(65) Prior Publication Data

US 2012/0197393 A1  Aug. 2, 2012

Related U.S. Application Data

(63) Continuation of application No. PCT/KR2010/001825, filed on Mar. 25, 2010.

(30) Foreign Application Priority Data

Oct. 16, 2009 (KR) .................. 10-2009-0098596

(51) Int. Cl.
*A61F 2/12* (2006.01)
*A61F 2/52* (2006.01)
*A61M 29/00* (2006.01)

(52) U.S. Cl.
USPC .................. 623/8; 623/7; 606/192

(58) Field of Classification Search
CPC .................. A61F 2/12; A61F 2/52
USPC .................. 623/8, 7; 606/192
See application file for complete search history.

(56) References Cited

U.S. PATENT DOCUMENTS

| | | | |
|---|---|---|---|
| 4,455,691 A * | 6/1984 | Van Aken Redinger et al. | 623/8 |
| 5,026,394 A * | 6/1991 | Baker | 623/8 |
| 5,630,844 A | 5/1997 | Dogan | |
| 6,074,421 A | 6/2000 | Murphy | |
| 6,162,251 A * | 12/2000 | Kredovski | 623/8 |
| 6,605,116 B2 | 8/2003 | Falcon | |
| 8,043,373 B2 * | 10/2011 | Schuessler et al. | 623/8 |
| 8,070,809 B2 * | 12/2011 | Schuessler | 623/8 |
| 2002/0143396 A1 * | 10/2002 | Falcon et al. | 623/8 |
| 2003/0018387 A1 * | 1/2003 | Schuessler | 623/8 |
| 2009/0030515 A1 * | 1/2009 | Schuessler et al. | 623/8 |
| 2009/0270985 A1 * | 10/2009 | Schuessler | 623/8 |
| 2010/0049316 A1 * | 2/2010 | Schuessler | 623/8 |
| 2010/0049317 A1 * | 2/2010 | Schuessler | 623/8 |
| 2010/0228347 A1 * | 9/2010 | Schuessler | 623/8 |
| 2011/0046729 A1 * | 2/2011 | Schuessler et al. | 623/8 |
| 2011/0230964 A1 * | 9/2011 | Yacoub et al. | 623/8 |
| 2011/0257743 A1 * | 10/2011 | Schuessler | 623/8 |
| 2011/0270392 A1 * | 11/2011 | Schuessler et al. | 623/8 |
| 2011/0276135 A1 * | 11/2011 | Yacoub et al. | 623/8 |

* cited by examiner

*Primary Examiner* — Andrew Iwamaye
(74) *Attorney, Agent, or Firm* — Park & Associates IP Law, P.C.

(57) ABSTRACT

The present invention relates to an artificial breast prosthesis which minimizes stress concentration and to a production method therefore, and more specifically relates to an artificial breast prosthesis which has excellent mechanical properties, superior tactile texture, and excellent safety and efficacy as a breast prosthesis, and also relates to a production method therefore. The artificial breast prosthesis made with the production method of the present invention, comprises a silicone shell which is of the same thickness as the connecting portion and has the same or similar physical properties thereof, and which minimizes the concentration of the stresses sustained after insertion into the body and maximizes resistance to fatigue failure such that durability is improved while at the same time the thinness of the connecting portion provides an outstanding texture to the prosthesis as a whole, and safety and efficiency are improved as stress concentration is minimized.

10 Claims, 3 Drawing Sheets

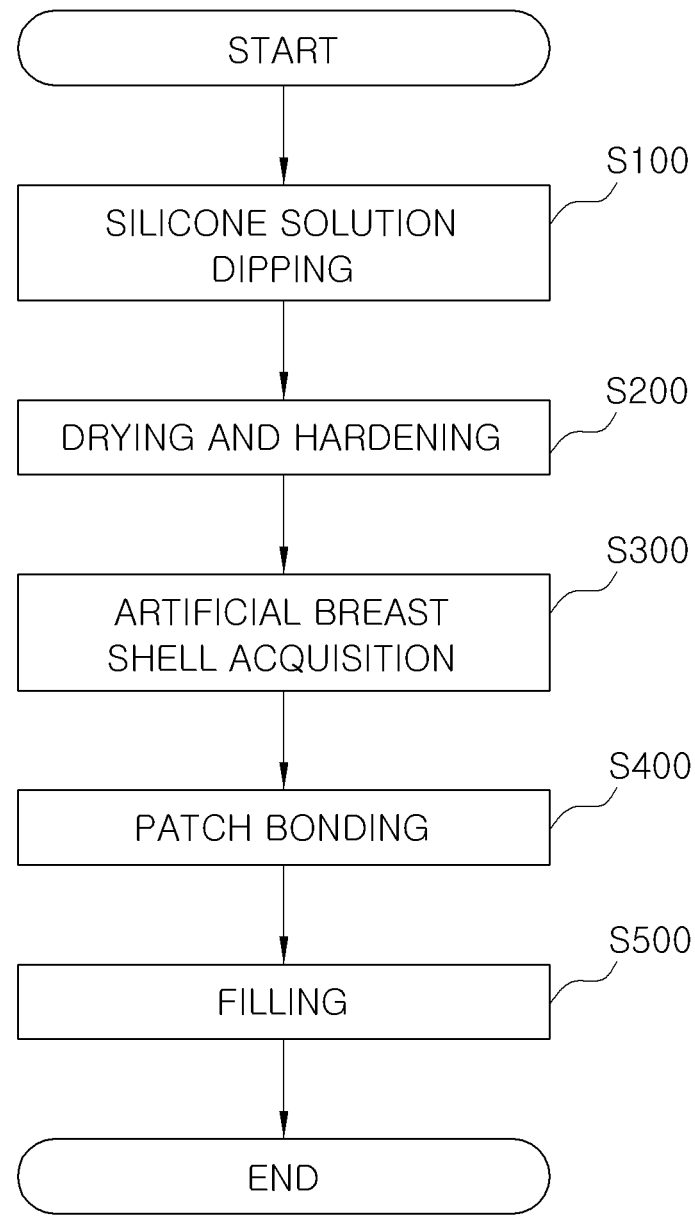

SILICONE ARTIFICIAL BREAST PROSTHESIS WHICH MINIMIZES STRESS CONCENTRATION, AND PRODUCTION METHOD THEREFOR

REFERENCE TO RELATED APPLICATIONS

This is a continuation of pending International Patent Application PCT/KR2010/001825 filed on Mar. 25, 2010, which designates the United States and claims priority of Korean Application No. 10-2009-0098596 filed on Oct. 16, 2009, the entire contents of which are incorporated herein by reference.

FIELD OF THE INVENTION

The present invention relates to an artificial breast prosthesis which minimizes stress concentration and a method for producing the same, and more particularly to an artificial breast prosthesis which has excellent mechanical properties, superior texture, and excellent safety and efficacy as a breast prosthesis, and a method for producing the same.

The artificial breast prosthesis, produced by the production method according to the present invention, includes a silicone shell having a constant thickness, and a bonding portion having the same or similar physical properties as the shell, thereby minimizing concentration of stress applied after the breast prosthesis is inserted into the human body, and maximizing resistance against fatigue failure and improving durability thereof, wherein the artificial breast prosthesis can achieve an outstanding texture owing to a small thickness of the bonding portion, and can improve safety and efficacy.

BACKGROUND OF THE INVENTION

In general, artificial breast prostheses are used in reconstructive plastic surgery for a breast when breast loss occurs due to diseases or accidents and in cosmetic surgery for a malformed breast. In terms of anatomy, artificial breast prostheses are also used for the substitution of organs or tissues.

Artificial breast prostheses are products in which a filling material, such as saline, hydro-gel, and silicone gel, is filled in an envelope formed of silicone that is implantable to an organ (hereinafter referred to as a "shell"). These artificial breast prostheses may be classified into round products and water drop shaped products according to the shape of a product, and may be classified into smooth products and textured products according to the surface conditions of a product. More particularly, the artificial breast prostheses will be described in brief as follows.

A saline filled artificial breast prosthesis is configured such that saline is injected or is injectable into a shell formed of silicone (more particularly, the shell being formed of polyorganosiloxane, such as polydimethylsiloxane or polydiphenylsiloxane). The saline filled artificial breast prosthesis has a structure consisting of a silicone shell and a valve.

Although the saline filled artificial breast prosthesis ensures safety of a user even if the filling material leaks into the human body after rupture of the shell as a result of using sterilized saline as the filling material, and is easy to change the volume of a breast by adjusting the injection amount of saline, the saline filled artificial breast prosthesis is significantly deteriorated to the touch after surgery as compared to other artificial breast prostheses and the shell thereof has inferior durability.

A hydro-gel filled artificial breast prosthesis is configured such that hydro-gel composed of monosaccharide and polysaccharides is filled within the same shell as that used in the above described saline filled artificial breast prosthesis. The hydro-gel filled artificial breast prosthesis is a product developed based on the principle that the filling material can be absorbed into and excreted from the human body even if the filling material leaks into the human body due to rupture of the shell.

However, in the case of the hydro-gel filled artificial breast prosthesis, safety with respect to long term use has not been established, volume change depending on the lapse of time and occurrence of wrinkles may increase after the artificial breast prosthesis is inserted into the human body, and feeling is unnatural as compared to a silicone gel filled artificial breast prosthesis. At present, the above described hydro-gel filled artificial breast prosthesis are not distributed in the market on the basis of the year 2000 due to problems in relation to the proof of safety.

A silicone gel filled artificial breast prosthesis is configured such that silicone gel having an appropriate viscosity is filled in a shell. The silicone gel filled artificial breast prosthesis has very superior product durability and more pleasant texture than the saline filled artificial breast prosthesis, and owing to these advantages, achieves a dominant position in the market. Although the Food and Drug Administration of the United States of America had imposed limitations on use of the silicone gel filled artificial breast prosthesis due to problems in relation to the proof of safety thereof, the use of the silicone gel filled artificial breast prosthesis was again allowed officially in the year 2006.

The silicone gel filled artificial breast prosthesis has been developed in the order of a first generation prosthesis, a second generation prosthesis, and a third generation prosthesis. This development history will be described in detail as follows.

The first generation silicone gel filled artificial breast prosthesis is a product sold from the middle of the 1960s to the middle of the 1970s, and was initially developed in the year 1961 by Cronin and Gerow. The first generation silicone gel filled artificial breast prosthesis can be represented in brief by the use of a thick shell, a smooth surface type, and silicone gel of a high viscosity. This prosthesis has caused gel bleed and capsular contracture, but a rupture speed thereof was relatively low due to the use of the thick shell.

The second generation silicone gel filled artificial breast prosthesis is a product sold from the middle of the 1970s to the middle of the 1980s, and includes a thin shell and a silicone gel filling material of a low viscosity, for the sake of smoother texture. This prosthesis is characterized by a similar gel bleed rate, higher rupture occurrence, and lower capsular contracture as compared to the first generation prosthesis.

The third generation silicone gel filled artificial breast prosthesis is a product sold from the middle of the 1980s to the present, and includes a gel bleed barrier layer to prevent gel bleed. The third generation silicone gel filled artificial breast prosthesis includes a thicker shell and silicone gel of a higher viscosity as compared to the second generation prosthesis. In addition, a product having a rough surface has been developed, in order to reduce capsular contracture.

The above described artificial breast prosthesis commonly include a shell, a bonding portion (hereinafter referred to as a "patch"), and a filling material.

Considering first the shell, most shells have been produced via a dipping method and have a limit in durability (in particular, against fatigue failure). Basically, the shell produced via a dipping method exhibits thickness deviation due to gravity, and this thickness deviation causes a portion of the shell to be relatively weak to stress.

The bonding portion (i.e. the patch) is formed using a patch to be bonded (i.e. a material to be placed over the shell), and a bonding material. In production of conventional artificial breast prostheses, the patch, which constitutes the bonding portion, has been formed of a material having the same thickness and same physical properties as the shell.

This is because although it is necessary to produce a multilayered patch which includes a barrier layer for preventing leakage of low molecular weight silicone in order to prevent strength deterioration of the patch, production of the multilayered thin film patch having a smaller thickness than the shell is commercially very difficult.

More specifically, as shown in FIGS. 1 and 2, in the case where a patch 6 having the same thickness as that of shells 5 and 7 (the average thickness of which is in a range of 500 μm to 800 μm) is used, bonding portions 8a and 8b are very thick and have lower expansibility. Further, stress concentration may occur due to a difference in physical properties at a boundary point between the shell and the bonding portion, which deteriorates durability against fatigue. As a result, rupture of the artificial breast prosthesis has very high occurrence frequency around the patch as known from clinical results.

SUMMARY OF THE INVENTION

Technical Problem

The present invention has been made in view of the above problems of the related art, and it is an object of the present invention to provide an artificial breast prosthesis with minimized stress concentration, in which a bonding portion is constructed such that a multilayered thin film patch, which includes a barrier layer for preventing leakage of low molecular weight silicone, and an additional patch, which allows the bonding portion to have the same or similar physical properties (expansibility, rigidity, elasticity, and the like) as a shell despite thickness deviation between the shell and the bonding portion, are bonded to each other via a bonding material, thereby preventing stress concentration due to a difference in physical properties at a boundary between the shell and the bonding portion, and consequently reducing occurrence of rupture that is the most serious defect of artificial breast prostheses, wherein the artificial breast prosthesis can achieve superior texture owing to the bonding portion having a small thickness, and can improve safety and efficacy.

Technical Solution

To solve the above described technical objects and in accordance with one embodiment of the present invention, a silicone gel filled artificial breast prosthesis with minimized stress concentration is characterized in that a bonding portion formed at a hole perforated in a lower end of a shell has a double patch bonding structure in which a multilayered thin film patch, which includes a barrier layer for preventing leakage of low molecular weight silicone, and a physical property complementary patch, which allows the bonding portion to have the same or similar physical properties as the shell despite thickness deviation between the shell and the bonding portion, are bonded to each other via a bonding material.

Further, according to another aspect of the present invention, a method for producing a silicone gel filled artificial breast prosthesis with minimized stress concentration includes a silicone solution dipping operation for dipping a breast shaped mold into a silicone solution to obtain an artificial breast shell; a drying and hardening operation for drying and hardening the artificial breast shell attached to the mold using a drier, to obtain a silicone artificial breast shell; an artificial breast shell acquisition operation for perforating a hole in a lower end of the artificial breast shell attached to the mold and detaching the artificial breast shell from the mold; a patch bonding operation for forming a double patch bonding structure by bonding a multilayered thin film patch, which includes a barrier layer for preventing leakage of low molecular weight silicone, and a physical property complementary patch, which allows a bonding portion to have the same or similar physical properties as the shell despite thickness deviation between the shell and the bonding portion, to the hole of the detached artificial breast shell via a bonding material; and a filling operation for filling the shell, to which the patches have completely been bonded, with a filling material.

ADVANTAGEOUS EFFECTS

According to the present invention, in a silicone gel filled artificial breast prosthesis with minimized stress concentration, through provision of a double patch bonding structure in which a multilayered thin film patch, which includes a barrier layer for preventing leakage of low molecular weight silicone, and a physical property complementary patch, which allows a bonding portion to have the same or similar physical properties as a shell despite thickness deviation between the shell and the bonding portion, are bonded to each other via a bonding material, it is possible to ensure that the shell and the bonding portion have the same or similar physical properties, such as expansibility (elasticity) and rigidity, and to prevent stress concentration due to a difference in physical properties at a boundary between the shell and the bonding portion, and consequently reduce occurrence of rupture that is the most serious defect of artificial breast prostheses. In addition, the artificial breast prosthesis can achieve superior texture owing to a small patch thickness, and also can achieve improved safety and efficacy and maximized product lifespan.

BRIEF DESCRIPTION OF THE DRAWINGS

FIG. 5 is a flowchart illustrating a method for producing an artificial breast prosthesis with minimized stress concentration according to an exemplary embodiment of the present invention.

Figure 1:
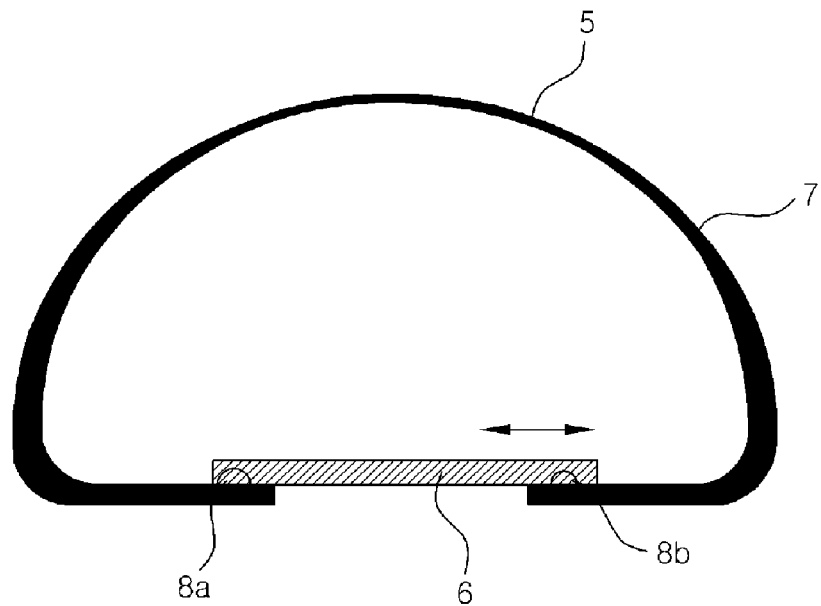
FIG. 1 is a view illustrating an artificial breast shell and a bonding portion of a conventional artificial breast prosthesis.
Figure 2:
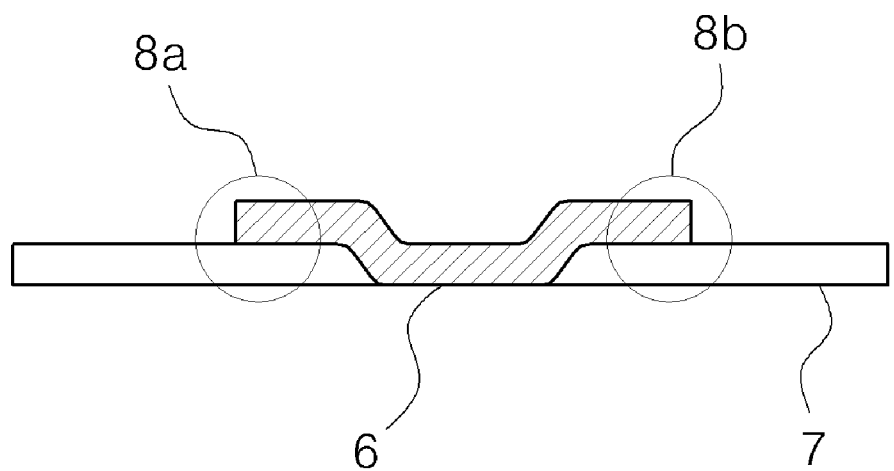
FIG. 2 is a view illustrating a silicon film bonded to the artificial breast shell of the conventional artificial breast shell.

Description of reference numerals about important parts of the drawings:
  10: artificial breast shell
  30: bonding boundary point
  50a: multilayered thin film patch
  50b: physical property complementary patch

DETAILED DESCRIPTION OF THE INVENTION

According to the present invention, a silicone gel filled artificial breast prosthesis with minimized stress concentration is characterized in that a bonding portion formed at a hole perforated in a lower end of a shell has a double patch bonding structure in which a multilayered thin film patch, which includes a barrier layer for preventing leakage of low molecular weight silicone, and a physical property complementary patch, which allows the bonding portion to have the same or similar physical properties as the shell despite thickness deviation between the shell and the bonding portion, are bonded to each other via a bonding material.

In this case, the multilayered thin film patch, including the barrier layer for preventing leakage of low molecular weight silicone, has a thickness of 100 μm or less, and the physical property complementary patch has a thickness in a range of 300 μm to 700 μm.

Further, according to the present invention, a method for producing a silicone gel filled artificial breast prosthesis with minimized stress concentration includes a silicone solution dipping operation S100 for dipping a breast shaped mold into a silicone solution to obtain an artificial breast shell; a drying and hardening operation S200 for drying and hardening the artificial breast shell attached to the mold using a drier, to obtain a silicone artificial breast shell; an artificial breast shell acquisition operation S300 for perforating a hole in a lower end of the artificial breast shell attached to the mold and detaching the artificial breast shell from the mold; a patch bonding operation S400 for forming a double patch bonding structure by bonding a multilayered thin film patch, which includes a barrier layer for preventing leakage of low molecular weight silicone, and a physical property complementary patch, which allows a bonding portion to have the same or similar physical properties as the shell despite thickness deviation between the shell and the bonding portion, to the hole of the detached artificial breast shell via a bonding material; and a filling operation S500 for filling the shell, to which the patches have completely been bonded, with a filling material.

In this case, in the artificial breast shell acquisition operation S300, when the hole is perforated in the lower end of the artificial breast shell, a cut cross section of the hole has an inclination angle of 30 degrees or less.

Hereinafter, the silicone gel filled artificial breast prosthesis with minimized stress concentration and the method for producing the same according to the present invention will be described in more detail.

Figure 3:
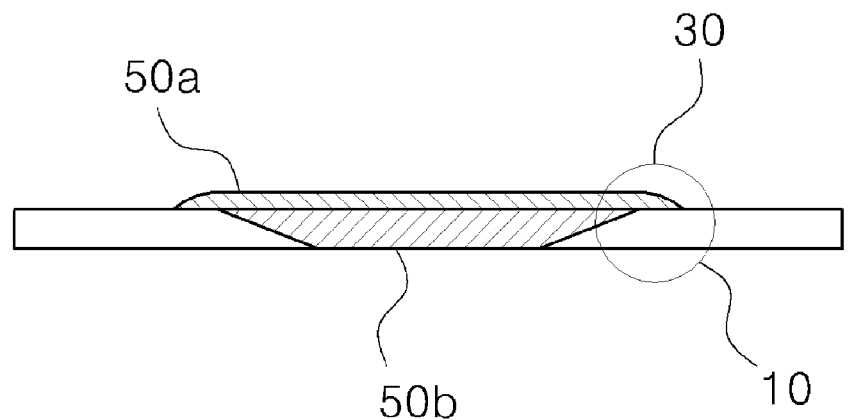
FIG. 3 is a view illustrating a bonding structure of a silicone gel filled artificial breast prosthesis with minimized stress concentration according to an exemplary embodiment of the present invention.

FIG. 3 is a view illustrating a bonding structure of a silicone gel filled artificial breast prosthesis with minimized stress concentration according to an exemplary embodiment of the present invention.

Figure 4:
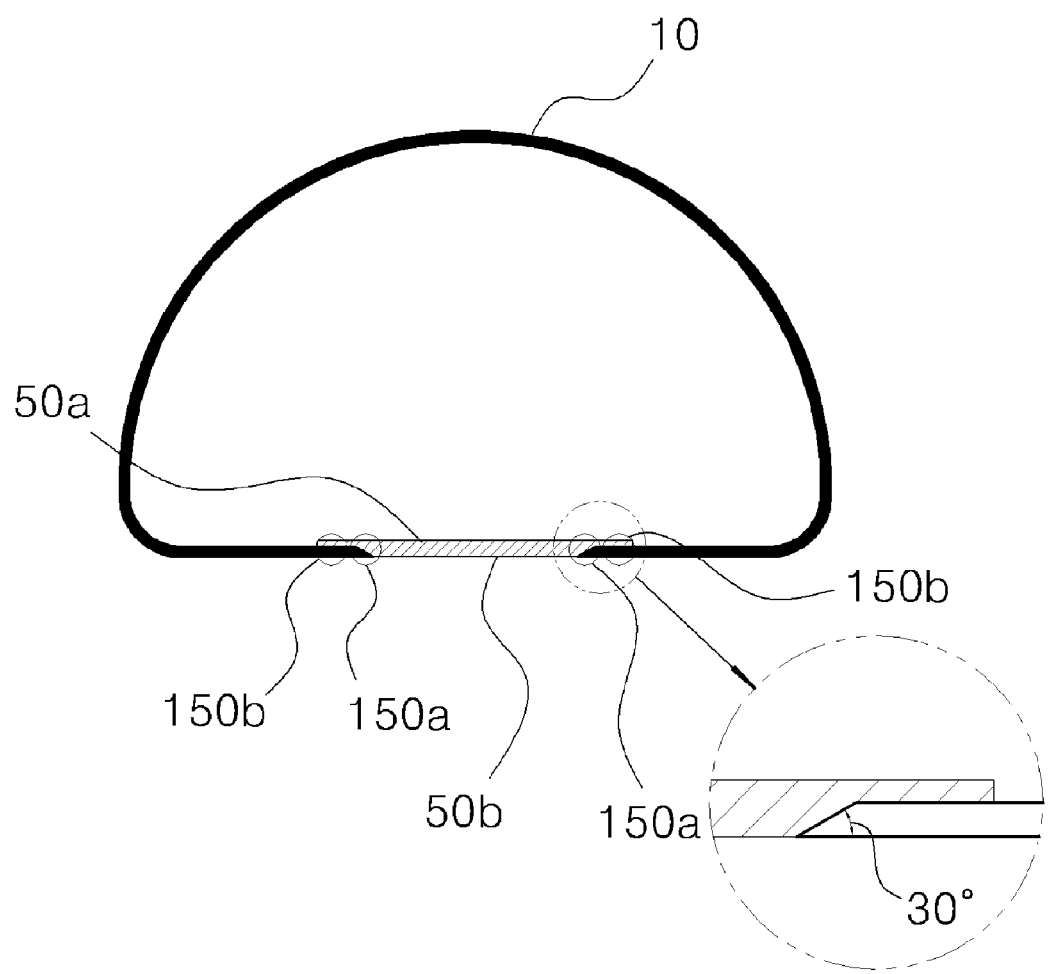
FIG. 4 is a view illustrating stress dispersion of the silicone gel filled artificial breast prosthesis with minimized stress concentration according to the exemplary embodiment of the present invention.

FIG. 4 is a view illustrating stress dispersion of the silicone gel filled artificial breast prosthesis with minimized stress concentration according to the exemplary embodiment of the present invention.

As shown in FIG. 3, the silicone gel filled artificial breast prosthesis with minimized stress concentration according to the present invention is characterized in that a bonding portion formed at a filling material injection hole has a double patch bonding structure in which a multilayered thin film patch 50a, which includes a barrier layer for preventing leakage of low molecular weight silicone, and a physical property complementary patch 50b, which allows the bonding portion to have the same or similar physical properties as the shell despite thickness deviation between the shell and the bonding portion, are bonded to each other via a bonding material.

Both the multilayered thin film patch 50a and the physical property complementary patch 50b are formed of polyorganosiloxane. Polyorganosiloxane available in the present invention is a class of an implant that can achieve safety after being implanted into the human body. In one example, a silica filler may be used.

In the present invention, the following materials are used.

Basically, polyorganosiloxane has a main chain of silane, and an organo group, such as a methyl group, is attached to the main chain of silane. As the most representative example of polyorganosiloxane, there is polydimethylsiloxane in which a methyl group is attached to a main chain of silane. A methyl group of dimethylsiloxane as a monomer of polydimethylsiloxane is substitutable for an organo group, such as an alkyl group, a phenyl group, a vinyl group, and the like.

For example, dimethylsiloxane may be substituted for methyl hydrogen siloxane, methyl phenyl siloxane, diphenyl siloxane, dimethyl vinyl siloxane, tri-fluoro propyl siloxane, and the like, so that polymers obtained by polymerization of these monomers may be used. In addition, copolymers using oligomer composed of the aforementioned monomers may be used.

In particular, the multilayered thin film patch 50a is formed of silicone polymers, which have a stabilized structure owing to molecular orientation and high compactness, and strong bonding force between the polymers. A blocking film is laminated on an intermediate layer among silicone polymer layers of the patch 50a. The blocking film is formed of silicone elastomers so that silicone oil molecules having a low molecular weight are difficult to physically and chemically pass through the blocking film. In addition, although the thickness of the blocking film may be adjusted in various ways for the sake of blocking effects, the thickness of the barrier layer is preferably in a range of 10 μm to 80 μm in consideration of efficacy and safety.

In one example, if the multilayered thin film patch 50a is formed of polymers obtained by polymerization of polydiphenylsiloxane and polydimethylsiloxane, the blocking film laminated on the intermediate layer of the multilayered thin film patch 50a may be formed of silicone elastomers obtained by polymerization of methyl 3,3,3-trifluoropropylpolysiloxane and dimethylpolysiloxane.

The multilayered thin film patch 50a including the barrier layer for preventing leakage of low molecular weight silicone has a thickness of 100 μm or less, and the physical property complementary patch 50b has a thickness in a range of 300 μm to 700 μm.

Although the physical property complementary patch 50b, which allows the bonding portion to have the same or similar physical properties as the shell despite a thickness difference between the shell and the bonding portion (the combined structure), may be formed of silicone polymers as mentioned above in the present invention, the physical property complementary patch 50b may be formed of silicone materials having different physical properties from the multilayered thin film patch 50a or the shell. This serves to insure that the double patch bonding structure in which the multilayered thin film patch 50a and the physical property complementary patch 50b are bonded to each other, has the same or similar physical properties as the shell.

Specifically, as shown in FIG. 3, the double patch bonding structure is composed of the multilayered thin film patch 50a and the physical property complementary patch 50b bonded together, in which the physical property complementary patch 50b is received in and attached to the conical-shaped hole of the shell, and has a planar upper surface and a planar lower surface that are, respectively, flush with the upper surface and the lower surface of the shell where the hole is formed. Thus, the double patch bonding structure is somewhat thicker than the shell by the thickness of the multilayered thin film patch 50a. In order to insure the double patch bonding structure to have the same or similar physical properties as the shell, it is necessary for the physical property complementary patch 50b to be formed of a softer material than the silicone material constituting the shell.

To this end, the silicone materials used in the production of the multilayered thin film patch 50a, the physical property complementary patch 50b, and the shell may include silica fillers of different contents. In this way, by adjusting the contents of silica fillers of the silicone materials depending on thickness deviation between the shell and the bonding portion, it is possible to ensure that the shell and the bonding portion may have the same or similar physical properties despite thickness deviation therebetween.

For the same reason, moreover, by adjusting the contents of functional groups, such as a vinyl group, a phenyl group, and a fluoro group of the silicone materials used in the production of the multilayered thin film patch 50a, the physical property complementary patch 50b, and the shell, it is possible to ensure that the shell and the bonding portion have the same physical properties. Similarly, this can be achieved by adjusting the polymerization degree of the silicone materials.

In one example, if both the shell and the multilayered thin film patch are formed of polymers obtained by polymerization of polydimethylsiloxane and polydiphenylsiloxane each having a silica content of 25 to 30%, the physical property complementary patch 50b may be formed of polymers obtained by polymerization of polydimethylsiloxane and polydiphenylsiloxane each having a silica content of 5 to 20%, in consideration of the thickness of the bonding portion.

The bonding material for bonding between the multilayered thin film patch 50a, the physical property complementary patch 50b, and the silicone shell may be selected from among the aforementioned silicone materials according to the present invention, and may take the form of a silicone gum, or Liquid phase Silicone Rubber (LSR).

Considering stress applied to the double patch bonding structure consisting of the multilayered thin film patch 50a and the physical property complementary patch 50b, as shown in FIGS. 3 and 4, stress caused by a leftward or rightward tensile force and stress caused by a tensile force in a direction of the cut cross section (having an inclination angle of 30 degrees) of the hole are simultaneously applied to a bonding boundary point 30, which results in stress dispersion in two axes and allows the bonding boundary point to have the same expansibility as the silicone shell. As a result, the double patch bonding structure consisting of the multilayered thin film patch 50a and the physical property complementary patch 50b has the same effects as the integrally formed silicone shell.

In addition, the two axis stress dispersion according to the present invention provides a bonding structure capable of preventing breakage due to stress, thereby compensating for disadvantages of silicone having weakness in tearing strength. Further, the bonding structure using an inclination angle of 30 degrees or less may increase a cross sectional area of bonding portions 150a and 150b, and consequently may increase bonding force, resulting in enhanced durability of the patch bonding structure.

Accordingly, the double patch bonding structure consisting of the multilayered thin film patch 50a and the physical property complementary patch 50b according to the present invention can prevent stress concentration due to a difference in physical properties at the boundary between the shell and the bonding portion, thereby reducing occurrence of rupture as the most serious defect of artificial breast prostheses. In addition, the artificial breast prosthesis can achieve superior texture owing to the fact that the bonding portion has approximately the same thickness as the shell, and also can achieve improved safety and efficacy and maximized product lifespan.

As shown in FIG. 5, the method for producing the silicone gel filled artificial breast prosthesis according to the present invention includes a silicone solution dipping operation S100 for dipping a breast shaped mold into a silicone solution to obtain an artificial breast shell; a drying and hardening operation S200 for drying and hardening the artificial breast shell attached to the mold using a drier to obtain a silicone artificial breast shell; an artificial breast shell acquisition operation S300 for perforating a hole in a lower end of the artificial breast shell attached to the mold and detaching the artificial breast shell from the mold; a patch bonding operation S400 for forming a double patch bonding structure by bonding a multilayered thin film patch, which includes a barrier layer for preventing leakage of low molecular weight silicone, and a physical property complementary patch, which allows a bonding portion to have the same or similar physical properties as the shell despite thickness deviation between the shell and the bonding portion, to the hole of the detached artificial breast shell via a bonding material; and a filling operation S500 for filling the shell, to which the patches have completely been bonded, with a filling material.

In this case, in the artificial breast shell acquisition operation S300, when the hole is perforated in the lower end of the artificial breast shell, a cut cross section of the hole has an inclination angle of 30 degrees or less.

Explaining the method in more detail, in operation S100, the breast shaped mold is dipped into the silicone solution, to obtain an initial artificial breast shell.

In operation S200, the mold dipped in the silicone solution is dried and hardened to obtain a silicone artificial breast shell. For example, the artificial breast shell attached to the mold is subjected to drying and hardening using the drier.

Subsequently, in operation S300, the hole is perforated in the lower end of the artificial breast shell attached to the mold, and the artificial breast shell is detached from the mold. In this case, when perforating the hole in the lower end of the artificial breast shell, an inclination angle of the cut cross section is 30 degrees or less, which effectively increases a bonding area and durability against stress, and provides an aesthetically pleasing appearance by hiding the resulting bonding surface.

After the artificial breast shell is detached from the hole, in operation S400, to cover the corresponding hole, the double patch bonding structure, which consists of the multilayered thin film patch, which includes the barrier layer for preventing leakage of low molecular weight silicone, and the physical property complementary patch, is bonded to the hole via the bonding material.

To bond the double patch bonding structure to the hole, a silicone bonding device, such as a press, is used. When using a conventional bonding method as shown in FIG. 1, the bonding surfaces 8a and 8b maintain bonding strength only on a single axis. On the other hand, according to the bonding method of the present invention, as shown in FIG. 4, a plurality of bonding surfaces 150a and 150b can simultaneously maintain bonding strength on two axes other than the single axis of the conventional method. Here, the two axes include a horizontal direction and a direction of the cut cross section (having an inclination angle of 30 degrees). The two axes correspond to directions exhibiting the highest durability against stress actually applied to the prosthesis.

In addition, as shown in FIG. 1, in the conventional bonding structure, the bonding portion has a thickness of 1,000 μm to 2,000 μm, and the shell and the bonding portion have a remarkable difference in physical properties, causing high stress to be concentrated on a boundary between the shell and the bonding portion, which results in a portion of the shell weak to fatigue. On the other hand, as shown in FIG. 4, through the bonding structure according to the present invention, as a result of using the multilayered thin film patch having a thickness of 100 μm or less, it is possible to minimize thickness deviation between the shell and the bonding portion. Further, as a result of forming the double patch bonding structure by bonding the multilayered thin film patch and the physical property complementary patch having a thickness of 300 μm to 700 μm to each other via the bonding material, it is possible to ensure that the shell and the bonding portion have the same physical properties, whereby the resulting bonding structure according to the present invention is very resistant to stress. In this way, the bonding portion according to the present invention achieves strong bonding strength and high durability against stress despite a small thickness thereof.

The configuration and operation principles of the silicone bonding apparatus will be easily understood by those skilled in the art, and thus a detailed description thereof will be omitted herein.

Through the production method as described above, the bonding portion has a double patch bonding structure, which consists of the multilayered thin film path including the barrier layer for preventing leakage of low molecular weight silicone, and the physical property complementary patch, and has the same or similar physical properties as the shell despite thickness deviation between the shell and the bonding portion, thereby minimizing stress concentration and maximizing resistance to fatigue, which can reduce occurrence of rupture that is the most serious defect of artificial breast prostheses. Further, owing to the small thickness of the bonding portion, it is possible to achieve superior texture and improved safety and efficacy of the prosthesis, and to maximize product lifespan.

Those skilled in the art will appreciate that the above description can be implemented in other detailed embodiments without changing technical ideas or essential characteristics of the present invention. Therefore, it should be understood that the above described embodiments are given only by way of example and the present invention is not limited thereto.

Accordingly, the scope of the present invention is defined by the accompanying claims other than the above detailed description, and all modifications or alternatives deduced from the spirit and scope of the invention as defined by the claims and equivalent concepts thereof should be construed as being included in the scope of the present invention.

What is claimed is:

1. A silicone gel filled artificial breast prosthesis comprising:
   a shell formed of a silicone material and having a hole formed there-through at a lower area of the shell, the hole having a conical shape with a wider opening at an upper surface of the shell and a narrower opening at a lower surface of the shell;
   a physical property complementary patch received in and attached to the conical-shaped hole of the shell, the physical property complementary patch having a planar upper surface and a planar lower surface that are, respectively, flush with the upper surface and the lower surface of the shell where the hole is formed; and
   a multilayered thin film patch having a planar lower surface which is bonded to the planar upper surface of the physical property complementary patch and to the upper surface of the shell adjacent the hole, the multilayered thin film patch including a blocking film for preventing leakage of low molecular weight silicone,
   wherein the physical property complementary patch is formed of a material softer than the silicone material forming the shell such that a combined structure of the multilayered thin film patch and the physical property complementary patch minimizes a stress concentration at an area where the combined structure is attached to the shell, despite a thickness difference between the shell and the combined structure.

2. The prosthesis according to claim 1, wherein the multilayered thin film patch has a thickness of 100 μm or less, and the physical property complementary patch has a thickness in a range of 300 μm to 700 μm.

3. The prosthesis according to claim 1, wherein the blocking film is formed of silicone elastomers, the blocking film being laminated on an intermediate layer among silicone polymer layers of the multilayered thin film patch.

4. The prosthesis according to claim 3, wherein a thickness of the blocking film is in a range of 10 μm to 80 μm.

5. The prosthesis according to claim 3, wherein the blocking film is formed of silicone elastomers obtained by polymerization of methyl 3,3,3-trifluoropropylpolysiloxane and dimethylpolysiloxane.

6. The prosthesis according to claim 1, wherein the stress concentration at the area where the combined structure is attached to the shell is minimized by adjusting a content of a silica filler of a silicone material of the combined structure or the silicone material of the shell.

7. The prosthesis according to claim 1, wherein the stress concentration at the area where the combined structure is attached to the shell is minimized by adjusting a content of a vinyl group, a phenyl group, and a fluoro group of a silicone material of the combined structure or the silicone material of the shell.

8. The prosthesis according to claim 1, wherein the stress concentration at the area where the combined structure is attached to the shell is minimized by adjusting a polymerization degree of a silicone material of the combined structure or the silicone material of the shell.

9. The prosthesis according to claim 1, wherein the multilayered thin film patch is bonded to the planar upper surface of the physical property complementary patch by a silicone gum or Liquid phase Silicone Rubber (LSR).

10. The prosthesis according to claim 1, wherein the conical-shaped hole of the shell to which the physical property complementary patch is attached has a cut cross section with an inclination angle of 30 degrees to distribute stress in two axes and minimize the stress concentration therein.

* * * * *